United States Patent
Coffindaffer et al.

(10) Patent No.: US 7,537,775 B2
(45) Date of Patent: May 26, 2009

(54) LOW PH SKIN CARE COMPOSITIONS CONTAINING DEHYDROACETIC ACID

(75) Inventors: Timothy Woodrow Coffindaffer, Maineville, OH (US); Robert Bao Kim Ha, Hamilton, OH (US); Margaret Ann O'Donoghue, Monroe, OH (US); Larry Richard Robinson, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 451 days.

(21) Appl. No.: 11/339,282

(22) Filed: Jan. 25, 2006

(65) Prior Publication Data

US 2006/0165741 A1    Jul. 27, 2006

Related U.S. Application Data

(60) Provisional application No. 60/647,197, filed on Jan. 26, 2005.

(51) Int. Cl.
*A61K 8/02* (2006.01)
*C07D 309/00* (2006.01)

(52) U.S. Cl. .......... 424/401; 549/291; 514/159
(58) Field of Classification Search .......... 424/401; 549/291; 514/159
See application file for complete search history.

(56) References Cited

U.S. PATENT DOCUMENTS 5,612,324 A * 3/1997 Guang Lin et al. .......... 514/162
6,150,403 A * 11/2000 Biedermann et al. ........ 514/460

* cited by examiner

*Primary Examiner*—Gina C. Yu
(74) *Attorney, Agent, or Firm*—S. Robert Chuey; Juliet A. Jones; Brian M. Bolam

(57) ABSTRACT

Stable skin care compositions comprising dehydroacetic acid and a dermatologically acceptable carrier. The dermatologically acceptable carrier comprises at least one oil, said oil having a solubility in water of about 5% or less and a solubility parameter of from about 7 to about 15, and the dehydroacetic acid is distributed primarily into said oil. The compositions have a pH of about 4.5 and below.

18 Claims, No Drawings

LOW PH SKIN CARE COMPOSITIONS CONTAINING DEHYDROACETIC ACID

CROSS-REFERENCE TO RELATED APPLICATION(S)

This application claims the benefit of Provisional Application Ser. No. 60/647,197, filed Jan. 26, 2005.

FIELD OF THE INVENTION

The present invention relates to low-pH skin care compositions containing dehydroacetic acid, suitable for improving the appearance and condition of mammalian skin.

BACKGROUND OF THE INVENTION

The skin is subject to assault by a number of extrinsic and intrinsic factors. Extrinsic factors can include radiation, pollution, wind, heat and low humidity. Intrinsic factors include biochemical changes, and, for example, increased skin oil production. Any of these factors may result in visible deterioration of the skin's appearance. Excessive amounts of skin oil, or sebum, production may result in oily skin, a cosmetically unattractive and undesirable condition. There exists a continuing need, therefore, for improved skin protection and for reduction of the skin's oily appearance.

Many skin care actives are more effective at a low pH. For example, salicylic acid long has been recognized as an effective inhibitor of sebaceous gland activity and for other positive effects on the skin. Whereas salicylic acid may be formulated across a wide pH range, its effectiveness increases as the pH approaches 3.0 or below.

Dehydroacetic acid also has proven effective in improving skin texture and appearance, and has the additional benefit of reducing oily skin. See, for example, Biederman et al., U.S. Pat. No. 6,150,403. Attempts to formulate aqueous, low-pH skin care compositions containing dehydroacetic acid lead to the observation that the dehydroacetic acid begins to exhibit instability at a pH of below about 7.0. Therefore, a need remains for stable, low-pH skin care compositions to effect delivery of dehydroacetic acid, either alone or in combination with other low-pH skin care actives.

SUMMARY OF THE INVENTION

The present invention meets the aforementioned needs. It now has been discovered that dehydroacetic acid can be stabilized by the presence of oils that possess both an optimal solubility parameter and limited solubility in water. The present invention describes stable skin care compositions made by a process that utilizes the solubility parameter and the limited solubility in water to allow the dehydroacetic acid to be distributed primarily into the oil phase. This in turn stabilizes the dehydroacetic acid at a low pH. Therefore, the present invention satisfies the need for skin care compositions capable of delivering dehydroacetic acid into the skin, either alone or in combination with other skin care actives that are most effective at a low pH.

According to the first embodiment of the present invention, a stable composition is provided for improving the condition and appearance of mammalian skin. The composition comprises dehydroacetic acid and a dermatologically acceptable carrier. The dermatologically acceptable carrier contains at least one oil, wherein the oil has a solubility in water of about 5% or less and a solubility parameter of from about 7 to about 15. The dehydroacetic acid is distributed primarily into the oil phase, and the composition has a pH of about 4.5 and below. The compositions optionally are in the form of moisturizers, cleansers and combinations thereof.

In accordance with a second embodiment of the present invention, a stable composition is provided for improving the condition and appearance of mammalian skin and for reducing the appearance of oily skin, comprising dehydroacetic acid, a second skin care active, and a dermatologically acceptable carrier. The dermatologically acceptable carrier is in the form of an oil-in-water emulsion, wherein the oil has a solubility in water of about 5% or less and a solubility parameter of from about 7 to about 15. The dehydroacetic acid is distributed primarily into the oil phase, and the composition has a pH of about 4.5 and below. The compositions optionally are in the form of moisturizers, cleansers and combinations thereof.

Yet another embodiment provides for depositing the skin care compositions according to the first and second embodiments onto a substrate, such as a wipe.

Yet another embodiment provides a method for regulating the condition of mammalian skin. The method comprises the step of applying a stable, low-pH skin care composition containing dehydroacetic acid in a dermatologically acceptable carrier, as described in the present invention, to the mammalian skin.

In yet another embodiment of the present invention a process of stabilizing dehydroacetic acid at a low pH is provided. This process comprises the step of distributing the dehydroacetic acid primarily into the oil phase of an oil-in-water emulsion.

These and other aspects and advantages of the present invention will become evident to those skilled in the art from a reading of the following detailed description.

DETAILED DESCRIPTION OF THE INVENTION

Whereas the specification concludes with claims that particularly point out and distinctly claim the present invention, it is believed that the invention will be better understood from the following details.

The present invention describes skin care compositions in which dehydroacetic acid is stabilized at a pH of about 4.5 and below. Previous attempts to formulate low-pH compositions suitable for application to the skin lead to the observation that dehydroacetic acid begins to exhibit instability at a pH of below about 7.0. To effect stabilization of dehydroacetic acid, the compositions of the present invention include oils that have both an optimal solubility parameter and limited solubility in water. The present invention describes stable skin care compositions made by a procedure that utilizes this combination of properties to stabilize dehydroacetic acid in its active form at a low-pH.

The compositions of the present invention may take a variety of final forms, non-limiting examples of which include lotions, creams, liquids and solid forms. In one embodiment, the compositions are in the form of a lotion or a cream. Alternatively, the compositions are applied to a substrate, suitable for use at a later time.

The compositions of the present invention include both compositions that are intended to be left on the skin indefinitely, or "leave-on" compositions, and compositions which are intended to be removed from the skin. Removal may occur through a variety of means, for example wiping or rinsing off the skin. In one embodiment, the compositions of the present invention are in the form of a rinse-off composition. This rinse-off composition may be in the form of a liquid, or also may be in the form of a lotion, or "cleansing milk."

In addition to dehydroacetic acid, the compositions of the present invention optionally may contain other skin care actives that exhibit stability at a low pH. Non-limiting example of such ingredients include salicylic acid, alpha-hydroxyacids, beta-hydroxyacids, and combinations thereof.

Each of the above and additional elements is described herein.

In all embodiments of the present invention, all percentages are by weight of the total composition, unless specifically stated otherwise. All ratios are weight ratios, unless specifically stated otherwise. The number of significant digits conveys neither limitations on the indicated amounts nor on the accuracy of the measurements. All amounts indicating quantities, percentages, proportions and pH measurements are understood to be modified by the word "about" unless otherwise specifically indicated. All measurements are understood to be made at 25° C. and at ambient conditions, where "ambient conditions" means conditions under about one atmosphere of pressure and at about 50% relative humidity.

Herein, "low pH" means a pH of below about 7.0. All pH measurements are made by standard means that would be known to one skilled in the art. The term "pH of the composition," or other language describing the pH of the composition means the pH of the undiluted, neat composition, measured after the composition is cooled to 25° C., unless otherwise indicated. The pH of the compositions of the present invention is about 4.5 and below. Alternatively, the pH is from about 2.0 to about 4.0. Alternatively, the pH is from about 2.5 to about 3.5. Alternatively, the pH is from about 2.8 to about 3.2.

Herein, "stable" and "stability" mean compositions which are substantially unaltered in chemical or physical state. "Stability" further means that the compositions and the skin care actives exhibit stability under reasonable shelf storage conditions, and under conditions reasonably expected to be incurred during transport and storage. Transport and storage conditions may include prolonged exposure to temperatures of from about −50° F. to about 150° F. Stability may be determined either by empirical observation or by appropriate methods of chemical analysis that would be known to one of skill in the art.

Herein, "skin care composition" means compositions suitable for topical application on mammalian skin and other keratinous tissue, for example, hair and nails. Topical means the surface of the skin and other keratinous tissue. Herein, "skin care" means regulating and improving skin condition. Herein, "regulating skin condition" means improving skin appearance and/or feel, for example, providing a smoother, more even appearance and/or feel. Herein, "skin care" may include reducing the oily and/or shiny appearance of skin, which means that one or more of the following benefits are achieved: there is a noticeable decrease in the visible oil, shine, greasiness, or highlights on the skin; the skin is substantially free from visible oiliness or shine; the skin has a substantially matte finish, or the user has a more uniform complexion.

I. Dehydroacetic Acid

Herein, "dehydroacetic acid" means the following compound:

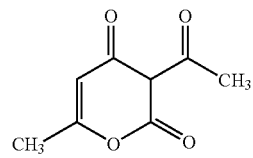

The technical name for dehydroacetic acid is 3-acetyl-6-methyl-2H-pyran-2,4,(3H)-dione, which can be commercially purchased from Tri-K Industries (Northvale, N.J.), and under the tradename GEOGARD® 221 or GEOGARD® 361 from Lonza (Annandale, N.J.). To make the compositions of the present invention, starting materials may include isomers, tautomers, salts and derivatives of dehydroacetic acid, which are converted to dehydroacetic acid upon distribution into the oil phase. In one embodiment, the compositions comprise from about 0.01% to about 5% dehydroacetic acid. Alternatively, the compositions include from about 0.05 to about 2% dehydroacetic acid. Alternatively, the compositions include from about 0.1% to about 1% dehydroacetic acid.

Dermatologically acceptable salts include alkali metal salts, such as sodium and potassium; alkaline earth metal salts, such as calcium and magnesium; non-toxic heavy metal salts; ammonium and trialkylammonium salts such as trimethylammonium and triethylammonium. Derivatives of dehydroacetic acid include, but are not limited to, any compounds wherein the $CH_3$ groups are individually or in combination replaced by amides, esters, amino groups, alkyls, and alcohol esters. Tautomers of dehydroacetic acid are the isomers of dehydroacetic acid which can change into one another with ease so that they ordinarily exist in equilibrium. Thus, tautomers of dehydroacetic acid can be described as having the chemical formula $C_8H_8O_4$ and generally having the structure above.

II. Dermatologically Acceptable Carrier

The topical compositions of the present invention also comprise a dermatologically acceptable carrier. Herein, the phrase "dermatologically acceptable carrier" means that the carrier is suitable for topical application to the keratinous tissue, has good aesthetic properties, is compatible with the actives of the present invention and any other components, and will not cause any safety or toxicity concerns. The compositions of the present invention comprise from about 50% to about 99.99% of the dermatologically acceptable carrier, alternatively from about 60% to about 99.9% of the carrier, alternatively from about 70% to about 98% of the carrier, and alternatively from about 80% to about 95% of the carrier.

The dermatologically acceptable carrier can be in a wide variety of forms. Non-limiting examples include simple solutions (water-based or oil-based), solid forms (for example, gels or sticks) and emulsions. Herein, "emulsions" generally contain an aqueous phase and a lipid or oil. Lipids and oils may be derived from animals, plants, or petroleum and may be natural or synthetic. Emulsion carriers include, but are not limited to, oil-in-water, water-in-oil, water-in-oil-in-water, and oil-in-water-in-silicone emulsions. In one embodiment, the dermatologically acceptable carrier comprises oil-in-water emulsions and water-in-oil emulsions. In yet another embodiment, the dermatologically acceptable carrier is an oil-in-water emulsion.

Oil

Oils suitable for use herein include any natural and synthetic oils with an overall solubility parameter of from about 7 to about 15, and which exhibit limited solubility in water. It is possible to use oils with higher solubility parameters than 15 and with lower solubility parameters than 7, if when the oils are blended with other oils, the weighted average of the solubility parameter of the oil blend is within the range of from about 7 to about 15. Herein, "weighted average" means that the volumes and the solubility parameters of the various oils are taken into account when calculating the average solubility parameter. Solubility parameters for the oils described herein are determined by methods known to one skilled in the chemical arts, and are expressed in units of (cal per $cm^3)^{1/2}$, where "cal" means calories and "$cm^3$" means cubic centimeters. Solubility parameters are discussed extensively by C. D. Vaughan in "The Solubility Parameter: What is it?" Cosmetics & Toiletries vol. 106, November, 1991, pp. 69-72, and also by C. D. Vaughan in "Using Solubility Parameters in Cosmetics Formulation", 36 J. Soc. Cosmetic Chemists 319-333, September/October, 1988.

The solubility parameter of the oils in the compositions of the present invention is from about 7 to about 15. Alternatively, the solubility parameter of the oils is from about 8 to about 14. Alternatively, the solubility parameter of the oils is from about 9 to about 12.

Herein, "solubility in water" means the extent to which the oil is dissolved in the water phase, where extent is expressed as the percentage of the total oil dissolved in the water. In the compositions of the present invention, the oil has a solubility in the water phase of about 5% or less.

Examples of suitable oils include, but are not limited to, polypropylene glycol-15 (PPG-15) stearylether, $C_{12-15}$ alkyl benzoate, butylphthalimide, isopropylphthalimide, available as PELEMOL BIP™ from Phoenix Chemical, Inc., caprylic/capric triglyceride, isopropyl N-lauroylsarcosinate, available as ELDEW™ SL 205, octylsalicylate, octylmethoxycinnamate, and mixtures thereof. Other examples of compounds with suitable solubility parameters are described in C. D. Vaughan, "Solubility Effects in Product, Package, Penetration and Preservation," *Cosmetics and Toiletries*, Vol. 103, October 1988, pp. 47-69.

In a preferred embodiment, the oil is PPG-15 stearylether, which has the following structure:

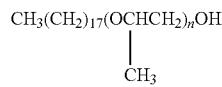

where "n" means that the average number of propylene glycol units is 15. In the present invention, the dehydroacetic acid is distributed primarily into the oil phase of the oil-in-water emulsion. As used herein, "distributed primarily" means that the dehydroacetic acid is substantially present in the oil phase, and is present only in minimal or undetectable amounts in the aqueous phase.

Emulsion

The compositions of the present invention may be in the form of an emulsion Emulsions may contain a humectant, for example, glycerin. Emulsions may further contain an emulsifier. Emulsifiers may be nonionic, anionic or cationic. Suitable emulsifiers are disclosed in, for example, U.S. Pat. No. 3,755,560 issued to Dickert et al., U.S. Pat. No. 4,421,769, issued to Dixon et al., and *McCutcheon's Detergents and Emulsifiers*, North American Edition, pages 317-324 (1986). Suitable emulsions may have a wide range of viscosities, depending on the desired product form.

III. Optional Ingredients

Skin Care Actives

The compositions of the present invention can further comprise one or more skin care actives capable of functioning in different ways to enhance the benefits of dehydroacetic acid and/or to provide other benefits. Non-limiting examples of these benefits include, but are not limited to enhancing the reduction of sebum synthesis, regulating the oily and/or shiny appearance of the skin, and providing anti-acne benefits.

The compositions of the present invention may contain salicylic acid, its isomers, tautomers, salts and derivatives thereof. Alternatively, the compositions comprise from about 0.001% to about 5% salicylic acid. Alternatively, the compositions comprise from about 0.01% to about 2% salicylic acid. Alternatively, the compositions comprise from about 0.1% to about 1% salicylic acid.

Dermatologically acceptable salts include alkali metal salts, such as sodium and potassium; alkaline earth metal salts, such as calcium and magnesium; non-toxic heavy metal salts; ammonium and trialkylammonium salts such as trimethylammonium and triethylammonium. Derivatives of salicylic acid include, but are not limited to, any compounds wherein the $CH_3$ groups are individually or in combination replaced by amides, esters, amino groups, alkyls, and alcohol esters. Tautomers of salicylic acid are the isomers of salicylic acid which can change into one another with ease so that they ordinarily exist in equilibrium. Thus, tautomers of salicylic acid can be described as having the chemical formula $C_7H_6O_3$ and generally having a similar structure to salicylic acid.

The compositions of the present invention may include from about 0.001% to about 5%, alternatively from about 0.01% to about 2%, and alternatively from about 0.1% to about 1%, of alpha- or beta-hydroxy acids, and derivatives, salts, isomers and tautomers thereof. Non-limiting examples of alpha- and beta-hydroxy acids include alpha-hydroxy-butyric acid, alpha-hydroxyisobutyric acid, alpha-hydroxyisocaproic acid, alpha-hydroxyisovaleric, atrolactic acid, beta-hydroxybutyric acid, beta-phenyl lactic acid, beta-phenylpyruvic acid, citric acid ethyl pyruvate, galacturonic acid, glucoheptonic acid, glucoheptono 1,4-lactone, gluconic acid, gluconolactone glucuronic acid, glucuronolactone, glycolic acid, isopropyl pyruvate, lactic acid, malic acid, amndelic acid, emthyl pyruvate, mucic acid, pyruvic acid, saccharic acid, saccharic acid 1,4-lactone, tartaric acid and tartronic acid, and mixtures thereof.

Surfactants

The compositions of the present invention may include one or more surfactants. These surfactants or combinations of surfactants should be mild, which means that these surfactants provide sufficient cleansing or detersive benefits but do not overly dry the skin. Surfactants useful herein include those selected from the group consisting of anionic surfactants, amphoteric surfactangs, zwitterionic surfactants, cationic surfactants, nonionic surfactants and mixtures thereof. Examples of such surfactants are found in and U.S. Pat. No. 5,624,666, issued to Coffindaffer et al. Concentrations of these surfactant are from about 0.1% to about 20%, alternatively from about 0.5% to about 15%, and alternatively from about 1% to about 10%.

Anionic surfactants useful in the compositions of the present invention are disclosed in McCutcheon's, *Detergents and Emulsifiers*, North American edition (1986), published by allured Publishing Corporation; McCutcheon's, Functional Materials, North American Edition (1992); and U.S. Pat. No. 3,929,678, issued to Laughlin et al. Non-limiting examples of anionic surfactants include those selected from the group consisting of sarcosinates, sulfates, sulfonates, isethionates, taurates, phosphates, lactylates, glutamates, and mixtures thereof. Other anionic materials useful herein are soaps (i.e., alkali metal salts, e.g., sodium or potassium salts) of fatty acids, typically having from about 8 to about 24 carbon atoms, alternatively from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853, cited above.

Amphoteric and zwitterionic detersive surfactants suitable for use in the compositions herein include those which are known for use in skin care, or other personal care cleansing. The concentration of such amphoteric or zwitterionic detersive surfactants in the compositions of the present invention are from about 0.1% to about 20%, alternatively from about 0.2% to about 10%, and alternatively from about 0.5% to about 5%. Non-limiting examples of suitable zwitterionic or amphoteric surfactants are described in U.S. Pat. Nos. 5,104,646 and 5,106,609, both issued to Bolich, Jr. et al.

Amphoteric detersive surfactants suitable for use in the compositions include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the compositions of the present invention are selected from the group consisting of cocoamphoacetate, cocoamphodiacetate, lauroamphoacetate, lauroamphodiacetate, and mixtures thereof. Commercially available amphoteric surfactants include those sold under the trade names MIRANOL® C2M Conc. N.P., MIRANOL® C2M Conc. O.P., MIRANOL® C2M SF, MIRANOL® CM Special, MIRANOL® Ultra (Rhodia, Inc.); ALKATERIC® 2CIB (Alkaril Chemicals); AMPHOTERGE® W-2 (Lonza, Inc.); MONATERIC® CDX-38, MONATERIC® CSH-32 (Mona Industries); REWOTERIC® AM-2C (Rewo Chemical Group); and SCHERCOTERIC® MS-2 (Scher Chemicals).

Zwitterionic detersive surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as a carboxy, sulfonate, sulfate, phosphate or phosphonate group. Preferred zwitterionic detersive surfactants are the betaines and sulfobetaines, for example, cocoamidopropylbetaine and cocoamidopropylhydroxy-sultaine.

The compositions of the present invention can comprise from about 0.1% to about 15%, alternatively from about 0.2% to about 10%, and alternatively from about 0.5% to about 5% of a cationic surfactant. Nonlimiting examples of cationic surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992). Without being limited by theory, it is believed that such cationic materials can also provide an antimicrobial effect to the compositions herein. Therefore, cationic materials having antimicrobial properties are highly useful herein.

Nonlimiting examples of cationic surfactants useful herein include cationic ammonium salts such as those having the formula:

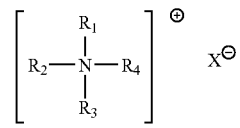

wherein $R_1$, is selected from an alkyl group having from about 12 to about 22 carbon atoms, or from aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 6 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain either linkages, or hydroxy or amino group substituents (e.g., the alkyl groups can contain polyethylene glycol and polyproylene glycol moieties).

The compositions of the present invention can comprise from about 0.1% to about 15%, alternatively from about 0.2% to about 10%, and alternatively from about 0.5% to about 5% of a nonionic surfactant. Nonlimiting examples of nonionic surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992).

Nonionic surfactants useful herein include those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include but are not limited to decyl alcohol, cetyl alcohol, stearyl alcohol, lauryl alcohol, myristyl alcohol, oleyl alcohol. Preferred examples of these surfactants include those wherein S is a glucose moiety, R is a C8-20 alkyl group, and n is an integer of from about 1 to about 9. Commercially available examples of these surfactants include decyl polyglucoside (available as APG 325CS™ from Henkel) and lauryl polyglucoside (available as APG 600CS™ and 625CS™ from Henkel). Other useful nonionic surfactants include the condensation products of alkylene oxides with fatty acids (i.e. alkylene oxide esters of fatty acids). Other nonionic surfactants are the condensation products of alkylene oxides with fatty alcohols (i.e. alkylene oxide ethers of fatty alcohols).

Particulate Materials

The present invention may comprise from about 0.1% to about 30%, alternatively from about 0.5% to about 15%, and alternatively from about 1% to about 5%, of particulate materials, including cleansing and exfoliating agents. The particulate cleansing or exfoliating agents can be derived from a wide variety of materials including those derived from inorganic, organic, natural, and synthetic sources. Non-limiting examples of these materials include almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fuller's earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, TEFLON® (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are particles made from mixed polymers (e.g., copolymers, terpolymers, etc.), among such are polyethylene/polypropylene copolymer, polyethylene/propylene/isobutylene copolymer, polyethylene/styrene copolymer, and mixtures thereof. Typically, the polymeric and mixed polymeric particles are treated via an oxidation process to destroy, for example, impurities. The polymeric and mixed polymeric particles can also optionally be cross linked with a variety of common crosslinking agents, non-limiting examples including butadiene, divinyl benzene, methylenebisacrylamide, allyl ethers of sucrose, allyl ethers of pentaerythritol, and mixtures thereof. Other examples of useful particles include waxes and resins such as paraffins, carnuba wax, ozekerite wax, candellila wax, and urea-formaldehyde resins. When such waxes and resins are used herein it is important that these materials are solids at ambient and skin temperatures.

Conditioning Agents

The compositions of the present invention may comprise from about 0.1% to about 50%, alternatively from about 0.5% to about 30%, alternatively from about 1% to about 20%, alternatively from about 2% to 15%, of a conditioning agent. These conditioning agents include, but are not limited to, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, poly alpha olefins, hydrogenated polyisobutenes and combinations thereof.

Non-limiting examples of silicone oils suitable for use herein include dimethicone copolyol, dimethylpolysiloxane, diethylpolysiloxane, mixed $C_{1-30}$ alkyl polysiloxanes, phenyl dimethicone, dimethiconol, and combinations thereof. In one embodiment, the silicone oils are non-volatile silicone oils selected from the group consisting of dimethicone, dimethiconol, mixed $C_{1-30}$ alkyl polysiloxanes, silicone crosspolymers, and combinations thereof. These and other examples of silicone oils useful herein are described in U.S. Pat. No. 5,011,681, issued to Ciotti et al.

Non-limiting examples of silicone cross-polymers suitable for use herein include acrylate/bis-hydroxypropyl dimethicone crosspolymer, $C_{30-45}$ alkyl cetearyl dimethicone crosspolymer, acrylate/bis-hydroxypropyl dimethicone crosspolymer, $C_{30-45}$ alkyl cetearyl dimethicone crosspolymer, cetearyl dimethicone/vinyl dimethicone crosspolymer, dimethicone crosspolymer, dimethicone crosspolymer-3, dimethicone/phenyl vinyl dimethicone crosspolymer, dimethicone/vinyl dimethicone crosspolymer, diphenyl dimethicone crosspolymer, divinyldimethicone/dimethicone crosspolymer, polyethylene glycol (PEG)-10 dimethicone crosspolymer, PEG-12 dimethicone crosspolymer, PEG-10 dimethicone/vinyl dimethicone crosspolymer, PEG-10/lauryl dimethicone crosspolymer, PEG-15/lauryl dimethicone crosspolymer, trifluoropropyl dimethicone/trifluoropropyl divinyldimethicone crosspolymer, vinyl dimethicone/lauryl dimethicone crosspolymer, vinyldimethyl/trimethylsiloxysilicate stearyl dimethicone crosspolymer, polysilicone-11, and mixtures thereof.

Also useful herein are various $C_{1-30}$ monoesters and polyesters of sugars and related materials, for example, sucrose esters of fatty acids (SEFA).

A variety of emollients may be employed as conditioning agents. These emollients may be selected from one or more of the following classes: triglyceride esters acetoglyceride esters, alkyl esters of fatty acids having 10 to 20 carbon atoms, alkenyl esters of fatty acids having 10 to 20 carbon atoms, fatty acids having 10 to 20 carbon atoms, fatty alcohols having 10 to 20 carbon atoms, lanolin, polyhydric alcohol esters, wax esters, vegetable waxes, phospholipids, sterols, amides, isomers, salts, derivatives and mixtures thereof.

These and other suitable conditioning agents are exemplified in U.S. Pat. No. 5,997,890, issued to Sine et al.

Structuring Agent

The compositions of the present invention may contain a structuring agent. Structuring agents are especially preferred in the emulsions of the present invention, and still more preferred in the oil-in-water emulsions of the present invention. Without being limited by theory, it is believed that the structuring agent assists in providing Theological characteristics (for example yield and structural characteristics) to the composition which contribute to the stability of the composition. The compositions of the present invention comprise from about 0.1% to about 20%, alternatively from about 0.5% to about 10%, and alternatively from about 1% to about 5%, of one or more structuring agents.

In one embodiment, structuring agents have a hydrophilic lipophilic balance (HLB) of from about 1 to about 8 and have a melting point of at least about 45° C. Suitable structuring agents include, but are not limited to, saturated fatty alcohols having between 14 and 30 carbon atoms, saturated fatty alcohols having between 16 and 30 carbon atoms and containing from about 1 to about 5 moles of ethylene oxide, saturated diols having from about 16 to about 30 carbon atoms, saturated monoglycerol ethers having from about 16 to about 30 carbon atoms, saturated hydroxy fatty acids having from about 16 to about 30 carbon atoms, hydroxylated and nonhydroxylated saturated fatty acids having from about 14 to about 30 carbon atoms, saturated ethoxylated fatty acids having from about 14 to about 30 carbon atoms, saturated fatty amines having from about 14 to about 30 carbon atoms and from about 1 to about 5 moles of ethylene oxide, saturated glyceryl mono-esters having from about 14 to about 30 carbon atoms and with a monoglyceride content of at least 40%, saturated polyglycerol esters having from about 14 to about 30 carbon atoms, from about 1 to about 3 alkyl groups and from about 2 to about 3 saturated glycerol units, glyceryl mono-ethers having from about 14 to about 30 carbon atoms, sorbitan mono- and diesters having from about 14 to about 30 carbon atoms, saturated ethoxylated sorbitan mono- and diesters having from about 14 to about 30 carbon atoms and with about 1 to about 5 moles of ethylene oxide, saturated methyl glucoside esters having from about 14 to about 30 carbon atoms, saturated sucrose mono- and diesters having from about 14 to about 30 carbon atoms, saturated ethoxylated methyl glucoside esters having from about 14 to about 30 carbon atoms and having from about 1 to about 5 moles of ethylene oxide, saturated polyglucosides having from about 14 to about 30 carbon atoms and having an average of between 1 to 2 glucose units, and mixtures thereof.

The preferred structuring agents of the present invention are selected from the group consisting of stearic acid, palmitic acid, stearyl alcohol, cetyl alcohol, behenyl alcohol, palmitic acid, the polyethylene glycol ether of stearyl alcohol having an average of from about 1 to about 5 ethylene oxide units, the polyethylene glycol ether of cetyl alcohol having an average of from about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Still more preferred structuring agents are selected from the group consisting of stearic acid, palmitic acid, stearyl alcohol, cetyl alcohol, behenyl alcohol, steareth-2, and mixtures thereof.

Thickening Agent

The compositions of the present invention can contain from about 0.1% to about 5%, alternatively from about 0.1% to about 4%, and alternatively from about 0.25% to about 3%, of one or more thickening agents, including thickeners and gelling agents. Nonlimiting classes of thickening agents include crosslinked polyacrylate polymers, polyacrylamide polymers, polysaccharides and gums. In one embodiment, the compositions of the present invention include a thickening agent selected from carboxylic acid polymers, crosslinked polyacrylate polymers, polyacrylamide polymers, and mixtures thereof. In yet another embodiment, the thickening agent is selected from carboxylic acid polymers, polyacrylamide polymers, and mixtures thereof.

Crosslinked polyacrylate polymers can include cationic polymers, nonionic polymers, and mixtures thereof. More preferred are cationic polymers. Examples of useful crosslinked polyacrylate nonionic and cationic polymers are those described in U.S. Pat. No. 5,100,660, issued to Hawe et al.; U.S. Pat. No. 4,849,484, issued to Heard; U.S. Pat. No. 4,835,206, issued to Farrar et al.; U.S. Pat. No. 4,628,078, issued to Glover et al.; U.S. Pat. No. 4,599,379, issued to Flesher et al.; and EP 228,868, issued to Farrar et al.

The compositions of the present invention can contain polyacrylamide polymers. More preferred are nonionic polyacrylamide polymers, which include substituted branched or unbranched polymers. More preferred among the nonionic polymers are isoparaffin and laureth-7, available under the Tradename SEPIGEL™ 305 from Seppic Corporation (Fairfield, N.J.). Other polyacrylamide polymers useful herein include multi-block copolymers of acrylamides, substituted acrylamides with acrylic acids, substituted acrylic acids and mixtures thereof. Commercially available examples of these multi-block copolymers include HYPAN™ SR150H, SS500V, SS500W, SSSA100H, from Lipo Chemicals, Inc. (Patterson, N.J.).

As used herein, "polysaccharides" refers to gelling agents which contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses, wherein the hydroxy groups of the cellulose polymer are hydroxyalkylated (for example, hydroxyethylated or hydroxypropylated) to form a hydroxyalkylated cellulose, which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, sold under the tradename NATROSOL® CS Plus from Aqualon Corp. (Wilmington, Del.). Other useful polysaccharides include scleroglucans which are a linear chain of (1-3) linked glucose units and every three units a (1-6) linked glucose. A commercially available example of a scleroglucan is CLEAROGEL™ CS11 from Michel Mercier Products Inc. (Mountainside, N.J.).

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Substrates

The compositions of the present invention can be applied directly to the skin. Additionally or alternatively, the compositions can be applied with the use of a suitable applicator comprising a substrate material for releasably holding the composition. The compositions of the present invention are particularly suitable for use in combination with a substrate to effect personal cleansing, skin treatment, or other personal care uses. In a preferred embodiment, the composition is pre-combined with or deposited onto the substrate to form a wipe product, one example of which is a disposable wipe product. Herein, "wipe product" means a substrate and a composition of the present invention which are pre-combined for later use. Wipe products may be packaged in a relatively dry state, and wetted prior to use, or may be packaged having already been wetted. The compositions and wipe products are well-suited for use in treating the skin of the face, neck and hands. However, it is to be understood that the compositions and wipe products of the present invention are useful in other applications.

Suitable wipe substrates include, but are not limited to, nonwovens, films, foams, sponges, and combinations thereof. Preferred wipe substrates comprise a porous material which is capable of holding the composition within the pores of the substrate. Therefore, preferred substrates include nonwovens.

Techniques for combining wipe substrates with a cleansing or treating composition, and for their packaging, are well known in the art and are applicable to the present invention. In general, the wipe substrate is combined with the composition by one or more techniques involving coating, immersing, dipping, spraying, extruding. In general, the wipes are combined with an amount of the composition sufficient to provide good, effective skin treatment.

Additional Optional Ingredients

The compositions of the present invention can contain a wide variety of additional ingredients including skin and hair care actives that are used in conventional product types, provided that they do not unacceptably alter the benefits of the invention. When incorporated into the composition, these ingredients should be suitable for use in contact with mammalian keratinous tissue without undue toxicity, incompatibility, instability, allergic response, and the like, within the scope of sound judgment. The *International Cosmetic Ingredient Dictionary and Handbook*, 10$^{th}$ Edition (2004) describes a wide variety of non-limiting cosmetic and pharmaceutical ingredients commonly used in the skin care industry, which are suitable for use in the compositions of the present invention. Examples of these and similar non-dehydroacetic acid ingredient classes include: abrasives, absorbents, aesthetic components such as fragrances, pigments, colorings/colorants, essential oils, skin sensates, astringents (non-limiting examples of which include clove oil, menthol, camphor, eucalyptus oil, eugenol, menthyl lactate, witch hazel distillate), anti-acne agents, anti-wrinkle agents, anti-inflammatory agents, anti-atrophy agents, anti-caking agents, desquamation agents, antimicrobial and antifungal agents (non-limiting examples of which include methylchloroisothiazolinone/methylisothiazolinone, iodopropynyl butylcarbamate), antioxidants, retinoids, N-acyl amino acid compounds, oil control agents, binders, biological additives, buffering agents, bulking agents, chelating agents, colorants, cosmetic astringents, cosmetic biocides, denaturants, drug astringents, emollients, external analgesics, film formers or materials (for example, polymers) for aiding the film-forming properties or substantivity of the composition (non-limiting examples of which include copolymers of eicosene and vinyl pyrrolidone), opacifying agents, pH adjusters, propellants, reducing agents, skin bleaching and lightening agents, skin firming agents, skin soothing and/or healing agents and derivatives, amino sugars, and vitamins and derivatives thereof. It should be noted, however, that many materials may provide more than one benefit, or operate via more than one mode of action. Therefore, classifications herein are made for the sake of convenience and are not intended to limit the active to that particular application or applications listed.

IV. Methods of Use

The present invention provides for a method for regulating the condition of mammalian skin. Regulating skin condition means improving skin appearance and/or feel, for example, providing a smoother, more even appearance and/or feel, and is described in more detail above.

The method of regulating skin conditions comprises the step of topically applying to the skin and/or other keratinous tissue a safe and effective amount of a skin care composition of the present invention. Any part of the external portion of the skin can be treated. The amount of the composition applied, the frequency of application and the period of use will vary widely depending upon the level of components of a given composition and the level of regulation desired.

In one embodiment, regulating skin condition is practiced by applying a composition in the form of a lotion, cleansing milk, cream, gel, foam, ointment, paste, emulsion, tonic, cosmetic, or the like and by leaving said composition on the skin or other keratinous tissue to produce some aesthetic, prophylactic, therapeutic or other benefit (i.e., a "leave-on" composition). In another preferred embodiment, for example as with a cleansing milk, the composition may be rinsed, wiped, or otherwise removed from the skin or keratinous tissue after application.

The application of the present compositions may be done using the palms of the hands and/or fingers, or by using an implement (e.g., a cotton ball, swab, pad, etc.). Where the composition has been applied to a substrate, the application is by means of wiping, dabbing, scrubbing, or other suitable means, the skin or keratinous tissue with the substrate. Depending upon the form of the composition, the substrate containing the composition may be wetted prior to application.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Examples 1-8

Skin care compositions useful for cleansing and/or conditioning may be prepared by the following procedure described below and using the ingredients in Table 1. The compositions may be applied directly to the skin or may be applied to a substrate.

TABLE 1

| Ingredients | 1 | 2 | 3 | 4 | 5 | 6 | 7 | 8 |
|---|---|---|---|---|---|---|---|---|
| Phase I: | | | | | | | | |
| Water | 0.06 | 0.06 | 0.06 | 0.06 | 0.10 | 0.10 | 0.06 | 0.06 |
| Butylated PVP [4] | 0.03 | 0.03 | — | — | 0.05 | 0.05 | — | 0.03 |
| Phase II: | | | | | | | | |
| PPG-15 Stearyl Ether [9] | — | 3.5 | 1.5 | 2.0 | 3.5 | 1.5 | — | 1.5 |
| C12–15 Alkyl Benzoate [6] | 4.0 | — | — | 2.0 | — | — | 3.5 | 2.0 |
| Salicylic Acid | 0.5 | 0.5 | — | — | 0.5 | 0.5 | — | — |
| Citric Acid | — | — | 0.4 | 0.4 | — | — | 0.4 | 0.4 |
| Dehydroacetic Acid | 0.20 | 0.20 | — | — | 0.25 | 0.25 | 0.10 | 0.10 |
| Phase III: | | | | | | | | |
| Water | 0.20 | 0.30 | 0.30 | 0.20 | 0.30 | 0.30 | 0.20 | 0.20 |
| Decyl Glucoside | 0.10 | 0.15 | 0.15 | 0.10 | 0.15 | 0.15 | 0.10 | 0.10 |
| Isohexadecane | — | 3.5 | — | 2.0 | — | 3.5 | 2.5 | 5.0 |
| Vitamin E Acetate | 0.1 | 0.05 | 0.1 | 0.05 | 0.1 | 0.1 | 0.1 | 0.05 |
| Sucrose Polycottonseedate [3] | 0.5 | — | 1.0 | 0.5 | — | — | 0.75 | 0.5 |

TABLE 1-continued

| Ingredients | 1 | 2 | 3 | 4 | 5 | 6 | 7 | 8 |
|---|---|---|---|---|---|---|---|---|
| Butylphthalimide and Isopropylphthalimide [7] | — | — | 2.5 | — | — | 3.0 | — | 2.5 |
| Dimethicone and Dimethiconol [5] | 1.0 | 0.5 | 0.75 | 1.0 | 0.5 | 0.5 | 0.75 | 0.75 |
| Fragrance | 0.02 | 0.02 | 0.02 | 0.02 | 0.02 | 0.02 | 0.02 | 0.02 |
| Phase IV: | | | | | | | | |
| Water | | | | | | | | |
| Sodium salt of dehydroacetic acid | — | — | 0.05 | 0.05 | 0.01 | 0.01 | — | 0.05 |
| Glycerin | 0.5 | 0.5 | 1.0 | 0.5 | 1.0 | 1.0 | 1.0 | 0.5 |
| Menthol | 0.01 | 0.01 | — | — | — | — | 0.02 | 0.02 |
| Glyceryl Polymethacrylate [1] | — | — | — | 1.0 | — | — | 0.75 | — |
| Sodium Polyacryloyldimethyl Taurate and Isohexadecane and Sorbitan Oleate [2] | 0 | 1.5 | 1.5 | 0 | 0 | 0 | 1.25 | 0 |
| Polyacrylamide and C13–14 Isoparaffin and Laureth-7 [8] | — | — | — | 1.0 | 1.25 | 1.25 | 1.0 | — |
| Water | QS [10] to 100% | QS to 100% | QS to 100% | QS to 100% | QS to 100% | QS to 100% | QS to 100% | QS to 100% |

[1] LUBRAJEL ® CG (Guardian Laboratories)
[2] SIMULGEL ® 800 (Seppic)
[3] SEFA Cottonate ® (Procter &Gamble Chemicals)
[4] GANEX ® P-904(International Specialty)
[5] Dow Corning 1503 Fluid
[6] FINSOLV ® TN (Finetex, Inc.)
[7] PELEMOL ® BIP (Pheonix Chemical, Inc.)
[8] SEPIGEL ® 305 (Seppic)
[9] ARLAMOL E ® (Uniqema, Americas)
[10] Quantum sufficiens, or an amount sufficient to bring the final composition to its intended final volume.

Method of Making Examples 1-8:

Step 1:
Into a suitable container, add phase I ingredients and mix until clear.
Into another suitable container, add phase II ingredients while mixing with a propeller mixer. While mixing, heat this mixture to approximately 55° C. Continue mixing until the acid is completely dissolved. Cool mixture to 25° C.
Add phase I to Phase II while slowly mixing with a propeller until the mixture is uniform.

Step 2:
Into a suitable container equipped with a propeller mixer, add phase III ingredients as following:
 a. Mix water and decyl glucoside.
 b. While mixing water/decyl glucoside mixture, add the rest of phase III ingredients one at a time. Continue mixing until mixture is uniform.

Step 3:
Into a suitable container equipped with a propeller mixer, add phase IV ingredients one at a time while mixing. Continue mixing until mixture is smooth (not grainy).
While mixing, add the Phase I/Phase II mixture, followed by Phase III mixture, to Phase IV. Adjust the mixer speed to maintain adequate mixing.
While mixing, adjust the pH to 4.5 or below using a citric acid or sodium hydroxide solution.
Continue mixing until mixture is smooth and homogeneous.
The compositions may be delivered via dosing directly onto skin and, or by preparing a substrate with above shared formulations. When prepared for use with a substrate, the product may be applied and or coated onto the substrate at a rate of from about 1 gram of lotion per gram of substrate to about 8 grams of lotion per gram of substrate.

Examples 9-11

Skin care compositions useful for cleansing may be prepared by the following procedure described below and using the ingredients in Table 2. The compositions may be applied directly to the skin or may be applied to a substrate.

TABLE 2

| Ingredients | 9 | 10 | 11 |
|---|---|---|---|
| Phase A | | | |
| Water | QS 100 | QS 100 | QS 100 |
| Glycerin | 3 | 5 | 5 |
| Tetrasodium EDTA | 0.02 | 0.01 | 0.01 |
| Phase B | | | |
| PPG-15 Stearyl Ether | 4 | 5 | 5 |
| Stearyl Alcohol | 2.88 | 2.88 | 2.88 |
| Salicylic Acid | 2.0 | 2 | 2 |
| Cetyl Alcohol | 0.8 | 0.8 | 0.8 |
| Distearyl Dimethyl Ammonium Chloride | 1.5 | 1.5 | 1.5 |
| Steareth-21 | 0.5 | 0.5 | 0.5 |
| Behenyl Alcohol | 0.32 | 0.32 | 0.32 |
| PPG-30 | 0.25 | 0.25 | 0.25 |
| Steareth-2 | 0.25 | 0.25 | 0.25 |
| Dehydroacetic Acid | 0.20 | 0.50 | 0.50 |
| Phase C | | | |
| Oxidized Polyethylene Beads [1] | 1 | 1 | |
| Fragrance | 0.27 | 0.27 | 0.27 |
| Menthol | 0.05 | | |
| Phase D | | | |
| Cetyl Betaine | 2 | 2 | 2 |
| Sodium Lauryl Sulfate | 1 | 1 | 1 |

[1] Available as ACCUSCRUB ® TM 51 from Allied Signal Corporation

In a suitable vessel, heat the Phase A ingredients with stirring to about 75° C. In a separate vessel, heat the Phase B ingredients with stirring to about 75° C. Add Phase B to Phase A with mixing. Add the oxidized polyethylene beads slowly with mixing to prevent agglomeration. Add the fragrance and menthol with mixing. Cool the mixture to about 35° C. In a separate vessel, combine the Phase D ingredients and add to the remaining mixture with stirring. Adjust the pH to 4.5 or below using a citric acid or sodium hydroxide solution.

TABLE 3

Skin care compositions in the form of cleansers and cleansing milk may be prepared by the following procedure described below and using the ingredients in Table 3.

| Ingredient | 12 % w/w | 13 % w/w | 14 % w/w | 15 % w/w | 16 % w/w |
|---|---|---|---|---|---|
| Phase A: | | | | | |
| Water | QS. | QS. | QS. | QS. | QS. |
| Disodium EDTA | 0.025 | 0.025 | 0.025 | 0.025 | 0.025 |
| Glycerin | 7.000 | 7.000 | 7.000 | 7.000 | 7.000 |
| Ethyl Panthenol | 0.100 | 0.100 | 0.100 | 0.100 | 0.100 |
| Phase B: | | | | | |
| Cetearyl glucoside &Cetearyl Alcohol [1] | 0.500 | 0.500 | 0.500 | 0.500 | 0.500 |
| Steareth-21 [2] | 0.100 | 0.100 | 0.100 | 0.100 | 0.100 |
| Cetyl Alcohol | 0.300 | 0.300 | 0.300 | 0.300 | 0.300 |
| Stearyl Alcohol | 0.450 | 0.450 | 0.450 | 0.450 | 0.350 |
| Behenyl alcohol | 0.300 | 0.300 | 0.300 | 0.300 | 0.150 |
| Vitamin E Acetate | 0.100 | 0.100 | 0.100 | 0.100 | 0.100 |
| Titanium dioxide/Isohexadecane/Triethoxycaprylylsilane/Polyhydroxystearic acid [3] | 0.900 | 0.900 | 0.900 | 0.900 | 0.900 |
| Iron Oxide (C.I. 77492)/PPG-15 Stearyl Ether/Triethoxycaprylylsilane/Polyhydroxystearic acid [4] | 0.0155 | 0.0155 | 0.0155 | 0.0155 | 0.0155 |
| Iron Oxide (C.I. 77491)/PPG-15 Stearyl Ether/Triethoxycaprylylsilane/Polyhydroxystearic acid [5] | 0.0055 | 0.0055 | 0.0055 | 0.0055 | 0.0055 |
| Tocopherol Nicotinate | 0.025 | 0.025 | 0.025 | 0.025 | 0.025 |
| Polymethylsilsesquioxane [6] | 2.000 | 2.000 | 2.000 | 2.000 | — |
| PPG-15 Stearyl Ether [7] | 4.000 | 8.000 | 4.000 | 8.000 | 4.000 |
| Salicylic Acid | 0.010 | 5.000 | 0.010 | 5.000 | 0.010 |
| Dehydroacetic Acid | 0.050 | 2.000 | 2.000 | 0.050 | 0.050 |
| Phase C: | | | | | |
| Polyacrylamide/C13–14 Isoparafin and Laureth-7 [8] | 1.500 | 1.500 | — | — | 1.500 |
| Sodium Polyacryloldimethyl Taurate/Isohexadecane and Sobitan Oleate [9] | — | — | 2.000 | 2.000 | — |
| Phase D: | | | | | |
| DC-1503 (Dimethicone and Dimethiconol) [10] | 2.000 | 2.000 | 2.000 | 2.000 | — |
| DC-200 (Dimethicone Fluid 5 cst) [11] | 0.750 | 0.750 | 0.750 | 0.750 | 6.000 |
| DC-9041 (Dimethicone & Dimethicone cross polymer [12] | — | — | — | — | 7.500 |
| Phase E: | | | | | |
| Perfume | 0.200 | 0.200 | 0.200 | 0.200 | 0.200 |

| Ingredient | 17 % w/w | 18 % w/w | 19 % w/w |
|---|---|---|---|
| Phase A: | | | |
| Water | QS. | QS. | QS. |
| Disodium EDTA | 0.025 | 0.025 | 0.025 |
| Glycerin | 7.000 | 7.000 | 7.000 |
| Ethyl Panthenol | 0.100 | 0.100 | 0.100 |
| Phase B: | | | |
| Cetearyl glucoside &Cetearyl Alcohol [1] | 0.500 | 0.500 | 0.500 |
| Steareth-21 [2] | 0.100 | 0.100 | 0.100 |
| Cetyl Alcohol | 0.300 | 0.300 | 0.300 |
| Stearyl Alcohol | 0.350 | 0.350 | 0.350 |

TABLE 3-continued

Skin care compositions in the form of cleansers and cleansing milk may be prepared by the following procedure described below and using the ingredients in Table 3.

| | | | |
|---|---|---|---|
| Behenyl alcohol | 0.150 | 0.150 | 0.150 |
| Vitamin E Acetate | 0.100 | 0.100 | 0.100 |
| Titanium dioxide/ Isohexadecane/ Triethoxycaprylylsilane/ Polyhydroxystearic acid [3] | 0.900 | 0.900 | 0.900 |
| Iron Oxide (C.I. 77492)/ PPG-15 Stearyl Ether/Tri-ethoxy-caprylylsilane/ Polyhydroxystearic acid [4] | 0.0155 | 0.0155 | 0.0155 |
| Iron Oxide (C.I. 77491)/ PPG-15 Stearyl Ether/Tri-ethoxy-caprylylsilane/ Polyhydroxystearic acid [5] | 0.0055 | 0.0055 | 0.0055 |
| Tocopherol Nicotinate | 0.025 | 0.025 | 0.025 |
| Polymethylsilsesquioxane [6] | — | — | — |
| PPG-15 Stearyl Ether [7] | 8.000 | 4.000 | 8.000 |
| Salicylic Acid | 5.000 | 0.100 | 5.000 |
| Dehydroacetic Acid | 2.000 | 2.000 | 0.050 |
| Phase C: | | | |
| Polyacrylamide/C13–14 Isoparafin and Laureth-7 [8] | 1.500 | — | — |
| Sodium Polyacryloldimethyl Taurate/Isohexadecane and Sobitan Oleate [9] | — | 2.000 | 2.000 |
| Phase D: | | | |
| DC-1503 (Dimethicone and Dimethiconol) [10] | — | — | — |
| DC-200 (Dimethicone Fluid 5 cst) [11] | 6.000 | 6.000 | 6.000 |
| DC-9041 (Dimethicone & Dimethicone cross polymer [12] | 7.500 | 7.500 | 7.500 |
| Phase E: | | | |
| Perfume | 0.200 | 0.200 | 0.200 |

[1] EMULGADE ™68 (Cognis Corp.)
[2] BRIJ ™ 721 (Uniquema Corp.)
[3] PM1P75CSI (Kobo Corp.)
[4] PSEP50EYSI (Kobo Corp.)
[5] PSEP70 ERSI (Kobo Corp.)
[6] TOSPEARL ™ 2000 (GE Corp.)
[7] ARLAMOL ™ E (Uniquema Corp.)
[8] SEPIGEL ™ 305 (Seppic Inc.)
[9] SIMULGEL ™ 800 (Seppic Inc.)
[10] DC-1503 (Dow Corning Inc.)
[11] DC-200 (Dow Corning Inc.)
[12] DC-9041 (Dow Corning Inc.)

Procedure for Compositions in Table 3:

1. Add Phase A ingredients into a suitable container. While mixing with a propeller, heat this mixture to 70-75° C.
2. Add Phase B to a suitable container. While mixing, heat this mixture to 70-75° C.
3. Add phase D ingredients to a suitable container and mix with a propeller until it is homogeneous.
4. When both phases A and B reach 70-75° C., add phase B to A while mixing with a propeller.
5. Mill the mixture of A and B for 1-3 minutes using a Tekmar mill at 9000-15,000 rpm. Remove the Tekmar mill and replace with a propeller mixer.
6. While mixing and cooling the mixture of A and B add phase C to the batch. Add phase D to the batch.
7. While mixing with a propeller, cool the batch to 35-40° C., ensuring that the batch is smooth and homogeneous. Mill the batch for 1-3 minutes, using a Tekmar mill at 9000-15000 rpm. Adjust pH to approximately 4.5 or below using a citric acid or sodium hydroxide solution.
8. Transfer the batch to containers for storage.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stable skin care composition comprising:
   a) dehydroacetic acid; and
   b) a dermatologically acceptable carrier comprising at least one oil, said oil having a solubility in water of about 5% or less and a solubility parameter of from about 7 to about 15;

wherein said dehydroacetic acid is distributed primarily into said oil; and wherein said composition has a pH of from about 2.5 to about 3.5.

2. The skin care composition of claim 1, wherein said dehydroacetic acid is present in an amount of from about 0.01% to about 5% by weight of the composition.

3. The skin care composition of claim 2, wherein said dehydroacetic acid is present in an amount of from about 0.05% to about 2% by weight of the composition.

4. The skin care composition of claim 3, wherein said dehydroacetic acid is present in an amount of from about 0.1% to about 1% by weight of the composition.

5. The skin care composition of claim 1, wherein said oil has a solubility parameter of from about 8 to about 14.

6. The skin care composition of claim 5, wherein said oil has a solubility parameter of from about 9 to about 12.

7. The skin care composition of claim 1, wherein said oil is selected from the group consisting of PPG-15 stearylether, $C_{12-15}$ alkyl benzoate, butylphthalimide, isopropylphthalimide, caprylic/capric triglyceride, isopropyl N-lauroylsarcosinate, octylsalicylate, octylmethoxycinnamate, and mixtures thereof.

8. The skin care composition of claim 7, wherein said oil is PPG-15 stearylether.

9. The skin care composition of claim 1, wherein the composition has a pH of from about 2.8 to about 3.2.

10. The skin care composition of claim 1, wherein said dermatologically acceptable carrier is in the form of an oil-in-water emulsion.

11. The skin care composition of claim 1, wherein said composition further comprises a second skin care active selected from the group consisting of salicylic acid, alpha-hydroxyacids, beta-hydroxyacids, and mixtures thereof.

12. The skin care composition of claim 11, wherein said second skin care active is salicylic acid.

13. The skin care composition of claim 1, wherein said composition is deposited onto a substrate.

14. A stable skin care composition comprising:
a) dehydroacetic acid;
b) salicylic acid; and
c) a dermatologically acceptable carrier, comprising at least one oil, said oil having a solubility in water of about 5% or less and a solubility parameter of from about 9 to about 12;
wherein said dehydroacetic acid is distributed primarily into said oil; and wherein said composition has a pH of from about 2.5 to about 3.5.

15. The skin care composition of claim 14, wherein said oil is PPG-15 stearylether.

16. The skin care composition of claim 14, wherein said composition is deposited onto a substrate.

17. A method for regulating the condition of mammalian skin, comprising the step of applying to the skin a stable skin care composition comprising:
a) dehydroacetic acid; and
b) a dermatologically acceptable carrier comprising at least one oil, said oil having a solubility in water of about 5% or less and a solubility parameter of from about 7 to about 15;
wherein said dehydroacetic acid is distributed primarily into said oil; and wherein said composition has a pH of from about 2.5 to about 3.5.

18. The process of producing stable skin care compositions comprising dehydroacetic acid and a dermatologically acceptable carrier, comprising the steps of:
a. providing said dehydroacetic acid;
b. providing an oil having a solubility in water of about 5% or less and a solubility parameter of from about 7 to about 15;
c. distributing said dehydroacetic acid primarily into said oil; and
d. providing a dermatologically-acceptable carrier; and
e. combining said oil with said dermatologically-acceptable carrier to produce a skin care composition; and
f. adjusting the pH of said skin care composition to from about 2.5 to about 3.5.

* * * * *